(12) United States Patent
Yetik

(10) Patent No.: US 10,695,217 B2
(45) Date of Patent: Jun. 30, 2020

(54) SYSTEM TO PROVIDE HUMIDIFIED CONTROLLED HIGH PRESSURE AIR DURING OCULAR SURGERY

(71) Applicant: Huseyin Yetik, Istanbul (TR)

(72) Inventor: Huseyin Yetik, Istanbul (TR)

( * ) Notice: Subject to any disclaimer, the term of this patent is extended or adjusted under 35 U.S.C. 154(b) by 297 days.

(21) Appl. No.: 15/843,321

(22) Filed: Dec. 15, 2017

(65) Prior Publication Data

US 2019/0175403 A1 Jun. 13, 2019

(30) Foreign Application Priority Data

Dec. 12, 2017 (IN) .............................. 201711044570

(51) Int. Cl.
| | | |
|---|---|---|
| *A61F 9/007* | (2006.01) | |
| *A61G 13/10* | (2006.01) | |
| *A61F 9/00* | (2006.01) | |
| *A61F 9/008* | (2006.01) | |

(52) U.S. Cl.
CPC .......... *A61F 9/00781* (2013.01); *A61F 9/007* (2013.01); *A61G 13/108* (2013.01); *A61F 9/0008* (2013.01); *A61F 2009/00885* (2013.01)

(58) Field of Classification Search
CPC .... A61F 9/0008; A61F 9/007; A61F 9/00781; A61G 13/108; A61B 3/165; A61M 2210/0612
USPC ........................................................ 600/401
See application file for complete search history.

(56) References Cited

U.S. PATENT DOCUMENTS

| | | | | |
|---|---|---|---|---|
| 4,905,711 A | * | 3/1990 | Bennett ................... | A61F 9/007 128/869 |
| 2009/0233540 A1 | * | 9/2009 | Valentino ............. | A61G 13/108 454/322 |
| 2010/0234794 A1 | * | 9/2010 | Weadock ............. | A61G 13/108 604/20 |
| 2012/0296261 A1 | * | 11/2012 | Whitaker .............. | A61F 9/0008 604/20 |
| 2013/0245536 A1 | * | 9/2013 | Friedman ............... | A61K 41/00 604/20 |
| 2014/0020686 A1 | * | 1/2014 | Kristensson ......... | A61G 13/108 128/204.16 |
| 2015/0306136 A1 | * | 10/2015 | Meloni .................. | A61K 33/00 424/600 |
| 2016/0310758 A1 | * | 10/2016 | Friedman ............. | A61N 5/0624 |

* cited by examiner

*Primary Examiner* — Ryan A Reis
(74) *Attorney, Agent, or Firm* — Gearhart Law LLC.

(57) ABSTRACT

A system to provide high pressure air to the eye during ocular surgery. The system has an air tube, a piece 1, a piece 2 and a plurality of adjustable aperture. Piece 1 has a plurality of piece 1 air feeding tubes, a piece 1 adjustable apertures and a plurality of air ejecting nozzles. Piece 2 comprises a piece 2 air feeding tubes, a piece 2 adjustable aperture, a diameter controlled adjustable aperture and a plurality of valves. Both piece 1 and piece 2 are used separately or simultaneously. Piece 1 is used laterally and piece 2 is used vertically. A humidifies high pressure air is provided to piece 1 and piece 2 air feeding tubes by an air source. The high pressure air provided is humidified controlled high pressure air.

14 Claims, 5 Drawing Sheets

SYSTEM TO PROVIDE HUMIDIFIED CONTROLLED HIGH PRESSURE AIR DURING OCULAR SURGERY

CLAIM OF PRIORITY

This application is a United States non-provisional application, claiming priority to Indian Application no 201711044570 filed on Dec. 12, 2017, the disclosure of which is incorporated herein by reference in its entirety.

FIELD OF THE EMBODIMENTS

The embodiments herein generally relate to a field of surgical instruments and, more particularly, relates to a system to provide humidified controlled high pressure air during ocular surgery.

BACKGROUND OF THE EMBODIMENTS

Ocular disorder is a major problem throughout the world. The ocular disorder is affecting large number of people of all ages. The ocular disorders like myopia, hyperopia and presbyopia results in visual impairment and blindness. The more devastating conditions are glaucoma, ocular hypertension, macular degeneration, retinal detachment and retinal tears.

Many surgical procedures are employed to restore, preserve or improve the vision of the eye. Some of these procedures include cataract surgery and corneal transplantation. Both the procedures require a surgical incision into the tissues and compartments of the eye. An eye with a normal intraocular pressure of about 15 mm Hg. above atmospheric maintains a steady resistance to deforming forces before an incision has been made.

Even an eye with an intraocular pressure measuring zero relative to atmospheric pressure, before an incision is made into the intraocular compartments, offer considerable resistance to transiently applied forces by responding with a transient rise in intraocular pressure. However, an eye with a cut connecting internal compartments with the operating room space at ambient atmospheric pressure has lost most of its ability to resist deformation because the ocular tissues can flow out through the opening, unimpeded, as a deforming force is applied.

During ocular surgery one of the dangerous and complicated experiences during the eye surgery is the suprachoroidal hemorrhage or more advanced form that is expulsive hemorrhage. During the surgery the pressure inside the eye decrease to low level i.e. up to zero relative to atmospheric pressure. Intravascular pressure in the choroidal vessels starts decompensate and un-contracted intravascular pressure than ruptures the suprachoroidal vessel and causes uncontrolled high pressure bleeding to the suprachoroidal area, as a result red reflex is lost and eye becomes rocky hard and when the eye is not closed tightly suprachoroidal hemorrhage occurs that pushes all the contents of eye outside through the wounds that results in expulsive hemorrhage.

Though there are many patents that provide pressure to the eye during ocular surgery but all the solutions are very expensive and have complex system and although not mountable on the microscope so, there is a need to devolve a system that is cost effective and simple.

SUMMARY OF THE EMBODIMENTS

The invention overcomes the above problem by introducing a system to provide high pressure air during the ocular surgery. The high pressure maintains the pressure level inside the eye, so that Intravascular pressure in the choroidal vessels do not decompensate and un-contracted intravascular pressure do not ruptures the suprachoroidal vessel that prevents uncontrolled high pressure bleeding to the suprachoroidal area and expulsive hemorrhage.

In view of the foregoing, an embodiment herein provides a device to provide humidified controlled high pressure air during ocular surgery. The device comprises an air tube, a piece 1, a piece 2 and a plurality of air tube adjustable apertures. The piece 1 further comprises a plurality of piece 1 air feeding tubes, a plurality of piece 1 adjustable aperture and a plurality of air ejecting nozzles. The piece 2 further comprises a piece 2 air feeding tube, a piece 2 adjustable aperture, a diameter controlled adjustable aperture and a plurality of valves.

In one of the embodiment, each air ejecting nozzles has a separate on/off valve to adjust the humidified controlled high pressure ejecting airflow. In another embodiment, each valve controls the air ejection area for any degree of angle depending upon need of the surgical area. In an embodiment, the piece 1 is attached all around the surgical area of the operating eye. The piece 1 ejects air laterally and forms an air pressure bridge over the surgical area. In another embodiment, each air ejecting nozzle's valve of piece 1 is used to adjust the pressure of humidified controlled high pressure air.

In one of the embodiment, the adjustable aperture of piece 2 ejects the humidified controlled high pressure air to form an umbrella shape. In another embodiment, the diameter of umbrella shape humidified controlled high pressure air is defined by a light source. In an embodiment, the adjustable aperture of piece 2 is used to adjust the diameter of the humidified controlled high pressure air umbrella. In an embodiment, the adjustable aperture is manual and motorized controlled.

In one of the embodiment, the plurality of valve of piece 2 is used to adjust the pressure of humidified controlled high pressure air. In an embodiment, the piece 2 is mounted co-axially or para-axially on a surgical microscope during ocular surgery. In another embodiment, the device is adapted to produce the humidified controlled high pressure air. In an embodiment, the device uses humidified controlled high pressure air from an air source of operating room.

In one of the embodiment, the high pressure air is humidified controlled high pressure air. In another embodiment, the piece 1 is detachable from the air tube, when piece 2 is used during the ocular surgery. In an embodiment, the piece 2 is detachable from the air tube, when piece 1 is used during the ocular surgery. In another embodiment, both piece 1 and piece 2 are used simultaneously depending upon the requirement of the surgery.

An embodiment herein provides a method for providing high pressure air laterally over the surgical area during the ocular surgery. Firstly a piece 1 is mounted around an operating eye during the ocular surgery, secondly a high pressure air is provided to the plurality of piece 1 air feeding tube through an air tube by an air source and finally high pressure airflow is ejected through a plurality of air ejecting nozzles laterally over surgical area of the operating eye.

In one of the embodiment, each air ejecting nozzle has an on/off valve. In an embodiment each on/off valve controls the pressure of humidified controlled high pressure air. In another embodiment the air source is an air source of an operating room. In an embodiment, the high pressure air is humidified controlled high pressure air.

An embodiment herein provides a method for providing high pressure air vertically over the surgical area during the ocular surgery. Firstly a piece 2 is mounted over a surgical microscope, secondly a high pressure air is provided to the piece 2 air feeding tube through an air tube by an air source and finally high pressure air flow is ejected vertically through an adjustable aperture of the piece 2 over the surgical area of an operating eye.

In one of the embodiment, mounting of the piece 2 is co-axially or para-axially on a surgical microscope during ocular surgery. In another embodiment, the high pressure air is humidified controlled high pressure air.

An embodiment herein provides a method to provide high pressure air laterally and vertically over the surgical area of an operating eye. Firstly piece 1 is mounted laterally around an operating eye, secondly a piece 2 is mounted over a surgical microscope then a high pressure air is provided to the piece 1 and the piece 2 through an air source. Finally a high pressure airflow is ejected laterally through a plurality of air ejecting pieces over surgical area of the operating eye and a high pressure airflow is ejected vertically through an adjustable aperture of the piece 2 over the surgical area of an operating eye. In one of the embodiment, the high pressure air is humidified controlled high pressure air.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein achieve this by providing a system to provide high pressure air to the eye during ocular surgery.

Figure 1:
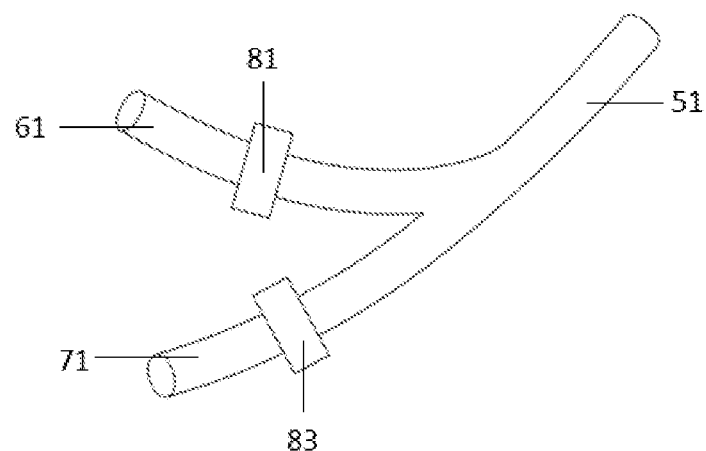
FIG. 1 illustrates the perspective view of a device of piece 1 and piece 2.

Here, the FIG. 1 describes a device to provide humidified controlled high pressure air during ocular surgery. The device comprises an air tube (51), a piece 1 (61), a piece 2 (71) and a plurality of air tube adjustable apertures (81, 83). Each air tube (51) adjustable apertures (81, 83) comprises a valve to control the opening and closing of piece 1 (61) and piece 2 (71). The humidified controlled high pressure air is passed through the air tube (51) by an air source. The air tube (51) then further ejects the humidified high pressure air to piece 1 (61) and piece 2 (71). The pressure of the humidified high pressure air is controlled by a plurality of apertures (81, 83). In case piece 1 (61) is working then the aperture (83) of piece 2 (71) is closed and in case piece 2 is working then the aperture (81) of piece 1 (61) is closed.

Figure 2:
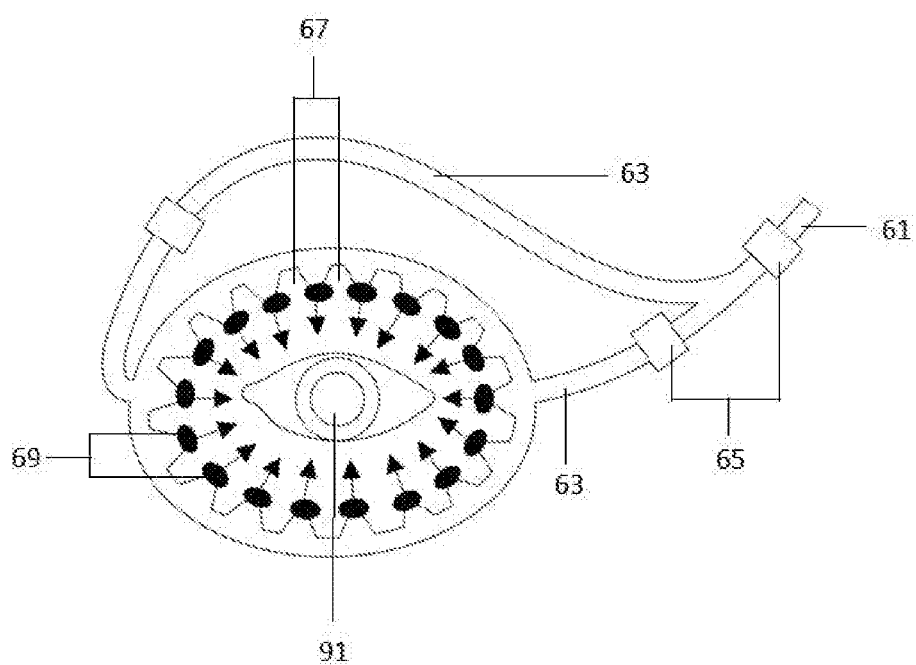
FIG. 2 illustrates the perspective view of piece 1.

FIG. 2 describes a piece 1 (61). The piece 1 (61) is used laterally. The piece 1 (61) comprises a plurality of piece 1 air feeding tubes (63), a plurality of piece 1 adjustable apertures (65) and a plurality of air ejecting nozzles (67). The piece 1 (61) is mounted laterally on the operated eye (91). The air is provided to the plurality of piece 1 (61) air feeding tubes (63) through an air tube (51) by an air source. Each air ejecting nozzles (67) has a separate on/off valve (69) to adjust the humidified controlled high pressure ejecting airflow.

Figure 3:
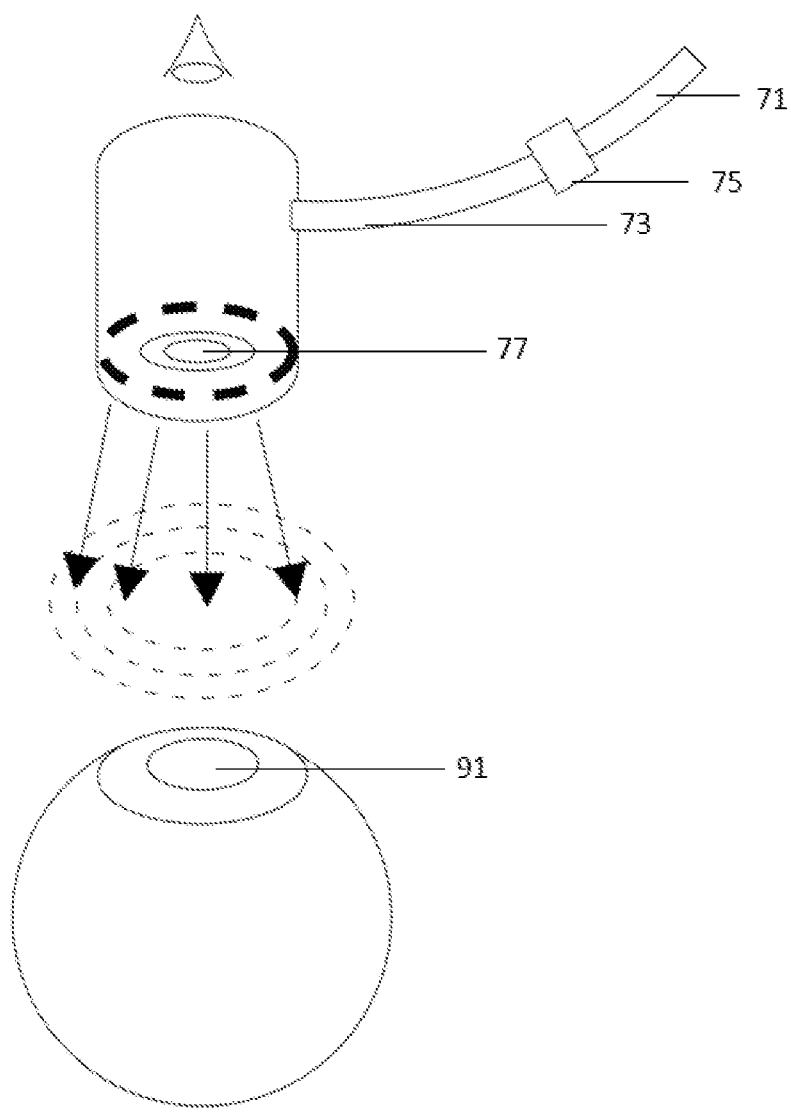
FIG. 3 illustrates the perspective view of piece 2.

FIG. 3 describes a piece 2 (71). The piece 2 (71) comprises a piece 2 air feeding tube (73), a piece 2 adjustable aperture (75), a diameter controlled adjustable aperture (77) and a plurality of valves, valves are located inside the aperture. The piece 2 (71) is mounted co-axially or para-axially on a surgical microscope during ocular surgery. The air is provided to piece 2 air feeding tube (73) through an air tube (51) by an air source. The piece 2 adjustable aperture (77) is used to control the pressure of humidified controlled high pressure air when the humidified controlled high pressure air is provided by the air tube (51). The diameter controlled adjustable aperture is used to control the diameter of the humidified controlled high pressure air. The plurality of vales controls the pressure of the humidified controlled high air pressure when the high pressure air is ejected to the eye (91) during surgery.

Figure 4:
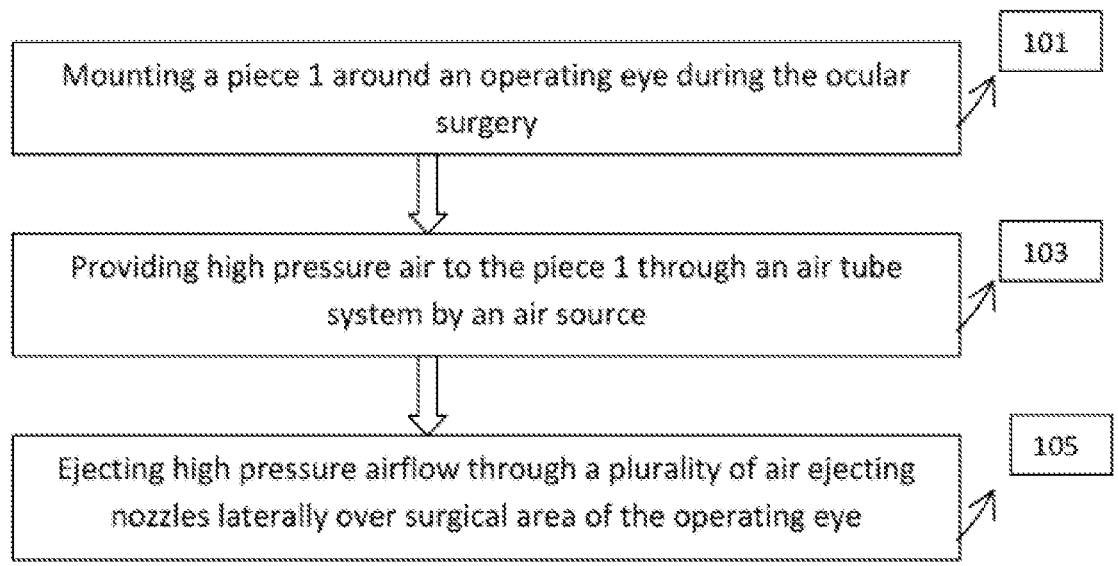
FIG. 4 illustrates a flow diagram of a method for providing high pressure air laterally over the surgical area during the ocular surgery.

FIG. 4 describes a method for providing high pressure air laterally over the surgical area during the ocular surgery. The method comprises following steps. In step 101, a piece 1 is mounted around an operating eye during the ocular surgery. In step 103, a high pressure air is provided to the piece 1 through an air tube system by an air source. In step 105, high pressure airflow is ejected through a plurality of air ejecting nozzles laterally over surgical area of the operating eye.

Figure 5:
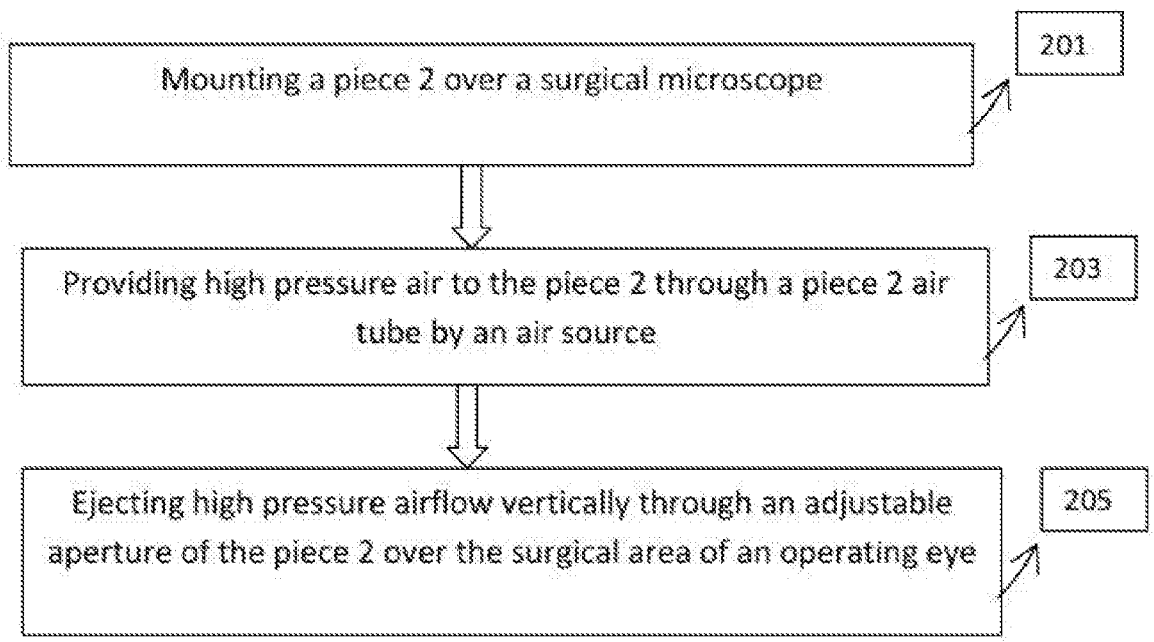
FIG. 5 illustrates a flow diagram of a method for providing high pressure air vertically over the surgical area during the ocular surgery.

FIG. 5 describes a method for providing high pressure air vertically over the surgical area during the ocular surgery. The method comprises followings steps. In step 201, a piece 2 is mounted over a surgical microscope. In step 203, a high pressure air is provided to the piece 2 through a piece 2 air tube by an air source. In step 205, high pressure airflow is ejected vertically through an adjustable aperture of the piece 2 over the surgical area of an operating eye.

Figure 6:
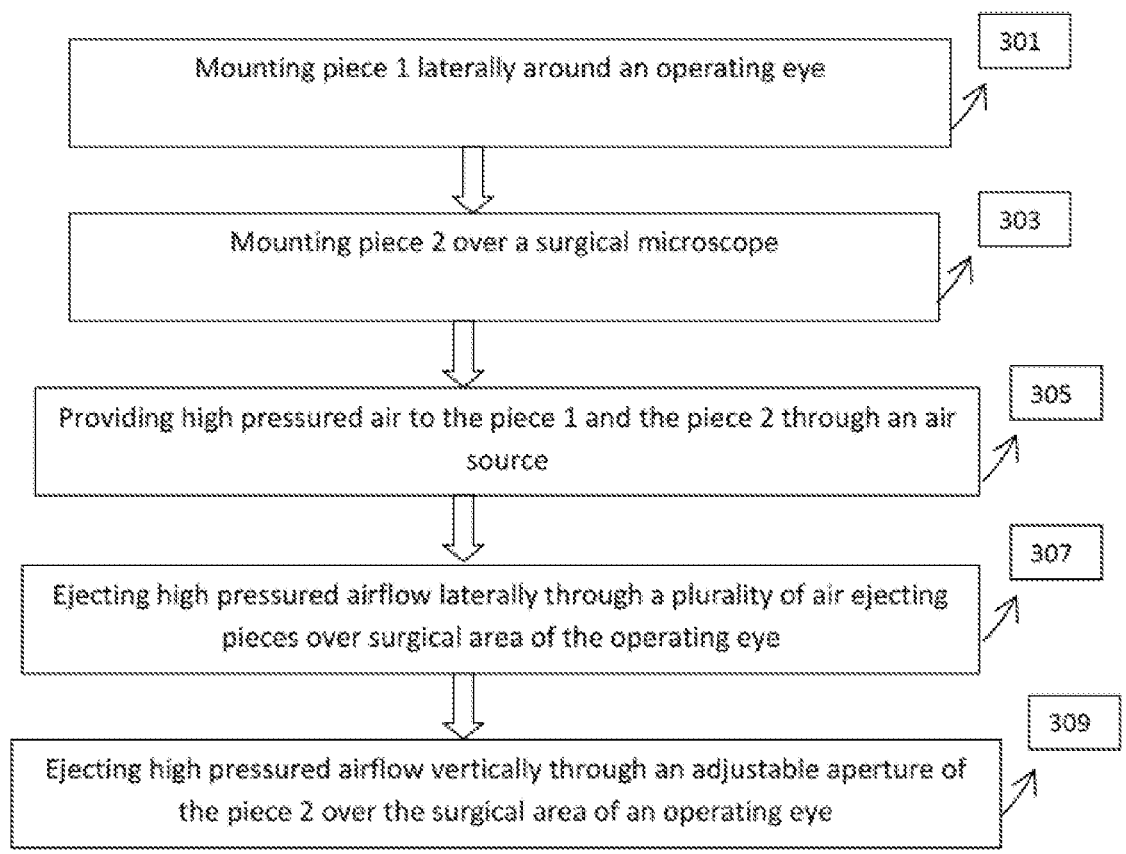
FIG. 6 illustrates a flow diagram of a method to provide high pressure air laterally and vertically over the surgical area of an operating eye.

FIG. 6 describes a method to provide high pressure air laterally and vertically over the surgical area of an operating eye. The method comprises following steps. In step 301, a piece 1 is mounted laterally around an operating eye. In step 303, piece 2 is mounted over a surgical microscope. In step 305, a high pressure air is provided to the piece 1 and the piece 2 through an air source. In step 307, a high pressure airflow is ejected laterally through a plurality of air ejecting pieces over surgical area of the operating eye. In step 309, high pressure airflow is ejected vertically through an adjustable aperture of the piece 2 over the surgical area of an operating eye.

Piece 2 has an additional hose pipe for focusing and condensing of the applied pressure air. The hose pipe is made of glass, plastic, acrylic etc. The hose pipe is re-usable and disposable. The parameters i.e. diameter of ejected humidified controlled high pressure air as well as the pressure level of humidified controlled high pressure air is controlled manually/motorized through a handle/pedal/button etc.

Piece 2 ejects the humidified controlled high pressure air to form an umbrella shape and the diameter of umbrella shape humidified controlled high pressure air is defined by a light source. A light is projected vertically on the surgical area so that the light is visible to the operator. Diameter or limits of high pressure applied area is visible by a simultaneously projected light. The light source is a laser light or any other equivalent that depicts the borders or whole area of applied high pressure. The device is re-usable and disposable, and is used sterile or non-sterile depending upon the situation.

As mentioned, there remains a need to develop a system that provides high pressure of air during ocular surgery without damaging the eye. The high pressure maintains the pressure level inside the eye, so that Intravascular pressure in the choroidal vessels do not decompensate and uncontracted intravascular pressure do not ruptures the suprachoroidal vessel that prevents uncontrolled high pressure bleeding to the suprachoroidal area and expulsive hemorrhage.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A device to provide a humidified controlled high pressure air during ocular surgery, the device comprising:
   an air tube, the air tube comprises:
   a piece 1, a piece 2 and a plurality of air tube adjustable apertures;
   each of the air tube adjustable apertures are located on the piece 1 and piece 2;
   the piece 1 further comprising:
   a plurality of piece 1 air feeding tubes;
   a plurality of piece 1 adjustable apertures; and
   a plurality of air ejecting nozzles,
   the piece 2 further comprising:
   a piece 2 air feeding tube;
   a piece 2 adjustable aperture;
   a diameter controlled adjustable aperture; and
   a plurality of valves located inside the diameter controlled adjustable aperture,
   wherein each of the air tube adjustable apertures comprises a valve to control the opening and closing of the piece 1 and the piece 2;
   the air tube allows humidified high pressure air to the piece 1 and the piece 2;
   the diameter controlled adjustable aperture controls the diameter of the humidified controlled high pressure air;
   each air ejecting nozzle has a separate an on/off valve, wherein each on/off valve is configured to control the pressure of humidified controlled high pressure air; and also control air ejection area for any degree of angle depending upon need of a surgical area; and
   the adjustable aperture of piece 2 ejects the humidified controlled high pressure air to form an umbrella shape, wherein the diameter of umbrella shape humidified controlled high pressure air is defined by a light source.

2. The device as claimed in claim 1, wherein the piece 1 is attached all around the surgical area of an operating eye, wherein the piece 1 ejects air laterally and forms an air pressure bridge over the surgical area.

3. The device as claimed in claim 1, wherein each of said air ejecting nozzle having said separate on/off valve of piece 1 is used to adjust the humidified controlled high pressure of air.

4. The device as claimed in claim 1, wherein the adjustable aperture of piece 2 is used to adjust the diameter of the humidified controlled high pressure air umbrella, wherein the adjustable aperture of the piece 2 is manual and motorized controlled.

5. The device as claimed in claim 1, wherein the plurality of valves of piece 2 are used to adjust the pressure of humidified controlled high pressure air.

6. The device as claimed in claim 1, wherein the piece 2 is mounted co-axially or para-axially on a surgical microscope during ocular surgery.

7. The device as claimed in claim 1, wherein the device is adapted to produce the humidified controlled high pressure air.

8. The device as claimed in claim 1, wherein the device uses humidified controlled high pressure air from an air source of an operating room.

9. The device as claimed in claim 1, wherein the piece 1 is detachable from the air tube, when piece 2 is used during an ocular surgery.

10. The device as claimed in claim 1, wherein the piece 2 is detachable from the air tube, when piece 1 is used during the ocular surgery.

11. The device as claimed in claim 1, wherein both the piece 1 and the piece 2 are used simultaneously depending upon requirement of the surgery.

12. A method for providing high pressure air laterally over a surgical area during an ocular surgery, the method comprising:
   mounting a piece 1 around an operating eye during the ocular surgery;
   providing high pressure air to the piece 1 through an air tube system by an air source; and
   ejecting high pressure airflow through a plurality of air ejecting nozzles laterally over surgical area of the operating eye;
   controlling pressure of humidified controlled high pressure air by a plurality of valves when high pressure air is ejected to the operating eye during the ocular surgery
   ejecting the humidified controlled high pressure air to form an umbrella shape, wherein diameter of the umbrella shape humidified controlled high pressure air is defined by a light source.

13. The method as claimed in claim 12, the method comprising:

mounting a piece 2 over a surgical microscope;

providing high pressure air to the piece 2 through a piece 2 air tube by the air source; and ejecting high pressure airflow vertically through an adjustable aperture of the piece 2 over the surgical area of an operating eye.

14. A method to provide high pressure air laterally and vertically over a surgical area of an operating eye, the method comprising:

mounting a piece 1 laterally around the operating eye;

mounting a piece 2 over a surgical microscope;

providing high pressure air to the piece 1 and the piece 2 through an air source;

ejecting high pressure airflow laterally through a plurality of air ejecting pieces over surgical area of the operating eye; and ejecting high pressure airflow vertically through an adjustable aperture of the piece 2 over the surgical area of the operating eye.

\* \* \* \* \*